(12) United States Patent
Stepp et al.

(10) Patent No.: US 9,200,013 B2
(45) Date of Patent: Dec. 1, 2015

(54) METHOD FOR PRODUCING SOLIDS FROM ALKALI SALTS OF SILANOLS

(71) Applicant: Wacker Chemie AG, Munich (DE)

(72) Inventors: Michael Stepp, Ueberackern (AT); Michael Mueller, Laufen (DE); Holger Wadewitz, Glaubitz (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 14/355,778

(22) PCT Filed: Nov. 13, 2012

(86) PCT No.: PCT/EP2012/072432
§ 371 (c)(1),
(2) Date: May 1, 2014

(87) PCT Pub. No.: WO2013/075969
PCT Pub. Date: May 30, 2013

(65) Prior Publication Data
US 2014/0296556 A1 Oct. 2, 2014

(30) Foreign Application Priority Data
Nov. 22, 2011 (DE) .......................... 10 2011 086 812

(51) Int. Cl.
*C07F 7/04* (2006.01)
*C07F 7/08* (2006.01)
*C07F 7/18* (2006.01)

(52) U.S. Cl.
CPC ................ *C07F 7/0836* (2013.01); *C07F 7/18* (2013.01)

(58) Field of Classification Search
CPC ................. C07F 7/0836; C07F 7/18
USPC .................................................. 556/465, 463
See application file for complete search history.

(56) References Cited

U.S. PATENT DOCUMENTS

| | | | |
|---|---|---|---|
| 2,438,055 A | 3/1948 | Hyde et al. | |
| 2,567,110 A | 9/1951 | Hyde | |
| 2,803,561 A | 8/1957 | Kather | |
| 5,856,546 A | 1/1999 | Graiver et al. | |
| 5,899,003 A * | 5/1999 | Strommen et al. | 34/363 |
| 6,842,422 B1 | 1/2005 | Bianchini, Jr. | |
| 2004/0096746 A1 | 5/2004 | Wietelmann et al. | |
| 2013/0145966 A1 | 6/2013 | Schildbach et al. | |
| 2014/0228589 A1 | 8/2014 | Stepp et al. | |

FOREIGN PATENT DOCUMENTS

| | | |
|---|---|---|
| DE | 1176137 | 8/1964 |
| DE | 4336600 C1 | 10/1994 |
| EP | 0650968 A1 | 5/1995 |
| EP | 2273221 A2 | 1/2011 |
| JP | 11-279183 A | 10/1999 |
| JP | 2004-511068 A | 4/2004 |
| JP | 2013-532639 A | 8/2013 |
| JP | 2014-530196 A | 11/2014 |
| WO | 02/28500 A1 | 4/2002 |
| WO | 20121022544 A1 | 2/2012 |

OTHER PUBLICATIONS

S. Vyzovkin C.A. Wright, "Model-Free and Model-Fitting Approaches to Kinetic Analysis of Isothermal and Nonisothermal Data" Thermochim. Acta, 1999 Elsevier Science, 340-341, 53-68.
Roduit, Ch. Borgeat, B. Berger, P. Folly, B. Alonso, J.N. Aebischer, F. Stoessel, "Advanced Kinetic Tools for the Evaluation of Decomposition Reactions", J Thermal Anal. And Calor. 2005, 80, 229-236.

* cited by examiner

*Primary Examiner* — Jafar Parsa
(74) *Attorney, Agent, or Firm* — Brooks Kushman P.C.

(57) ABSTRACT

Solid silanol salts are produced by drying an alkali siliconate solution in a fixed bed dryer containing solids.

18 Claims, No Drawings

METHOD FOR PRODUCING SOLIDS FROM ALKALI SALTS OF SILANOLS

CROSS-REFERECNE TO RELATED APPLICATIONS

This application is the U.S. National Phase of PCT appln. No. PCT/EP2012/072432 filed Nov. 13, 2012, which claims priority to German application DE 10 2011 086 812.7 filed Nov. 22, 2011, the disclosures of which are incorporated in their entirety by reference herein.

BACKGROUND OF THE INVENTION

1. Field of the Invention

The invention relates to a process for producing solids of silanol salts from alkoxysilanes, alkali metal hydroxide and water, in which water and alcohol are removed in a fixed bed.

2. Description of the Related Art

Alkali metal organosiliconates such as potassium methyl siliconate have already been in use for decades for hydrophobization, in particular of mineral construction materials. Owing to their good solubility in water they can be applied in the form of an aqueous solution to solids, where, after evaporation of the water, they form firmly adhering, permanently water-repellent surfaces under the influence of carbon dioxide. Since they comprise virtually no hydrolytically cleavable organic radicals, curing advantageously takes place without the release of undesirable volatile, organic secondary products.

The preparation of alkali metal organosiliconates, in particular potassium and sodium methyl siliconates, has been described many times. In most cases, the focus is on the preparation of ready-for-use and storage-stable, aqueous solutions. For example, DE 4336600 claims a continuous process starting from organotrichlorosilanes via the intermediate organotrialkoxysilane. Advantages of that process are that the secondary products hydrogen chloride and alcohol that form are recovered, and the siliconate solution that forms is virtually free of chlorine.

Ready-for-use construction material mixtures such as cement or gypsum renders and fillers or tile adhesives are mainly supplied to the construction site in the form of powders in bags or silos and are only mixed with the mixing water on site.

There is required for that purpose a solid hydrophobizing agent which can be added to the ready-for-use dry mixture and develops its hydrophobizing action in a short time only upon addition of water during application on site, for example on the construction site. This is called dry-mix application. Organosiliconates in solid form have proved to be very efficient hydrophobizing additives for that purpose. Their use is described, for example, in the following specifications:

Application PCT/EP2011/061766 claims solid organosiliconates having a reduced alkali metal content. Their preparation is carried out by hydrolysis of alkoxy- or halosilanes with aqueous alkali metal hydroxide solution and azeotropic drying of the resulting, optionally alcoholic-aqueous siliconate solution with the aid of an inert solvent as an entrainer.

U.S. Pat. No. 2,567,110 describes access to neutral (poly) siloxanes starting from alkali metal sil(ox)anolates and chlorosilanes. Example 1 describes the preparation of sodium methyl siliconate by reaction of a monomethylsiloxane hydrolyzate with a molar equivalent of sodium hydroxide solution in the presence of ethanol. The solid is isolated by distilling off the solvent and is then dried at 170° C. to a constant weight. Such a process for isolating solids is unworkable on an industrial scale because there, deposits that adhere firmly during the concentration by evaporation form on the walls of the reaction vessel.

A further disadvantage of the hitherto described processes of concentration by evaporation in the isolation of the solid is the fact that alkali metal siliconates decompose thermally, which constitutes a reaction safety problem. For example, potassium methyl siliconate (K:Si=1:1) decomposes above 120° C. in a highly exothermic reaction of 643 J/g with the loss of the methyl group. Under adiabatic conditions, the temperature rises to over 300° C. Consequently, it is also to be assumed that thermal decomposition occurs in the process claimed in DE 1176137 for drying an aqueous siliconate solution at 350-400° C. on a rotating hotplate. Irrespective thereof, such high temperatures require specific, expensive materials and complex safety measures in particular when flammable solvents are present. Moreover, starting from predominantly or purely aqueous solutions of the alkali metal siliconates, a very large amount of energy is required for the evaporation of the solvent water, which impairs the economy of the process or is too complex in terms of apparatus for conversion to an industrial scale.

U.S. Pat. No. 2,438,055 describes the preparation of siliconates as hydrates in solid form. In that document, the hydrolyzate of a monoorganotrialkoxysilane or of a monoorganotrichlorosilane is reacted with 1-3 molar equivalents of alkali metal hydroxide in the presence of alcohol. The siliconates formed as hydrates are crystallized out by evaporating off the alcohol or by adding corresponding non-polar solvents. In Example 1, the preparation of solid sodium methyl siliconate hydrates is described: to that end, 1 molar equivalent of methyltriethoxy-silane is reacted with 1 molar equivalent of sodium hydroxide in the form of saturated sodium hydroxide solution (i.e. 50 wt. %). Methanol is added to the solution in order to crystallize the siliconate. Evidently only a portion of the siliconate thereby precipitates. In fact, a further solid is isolated by concentration of the mother liquor by evaporation, which solid exhibits a 21% weight loss upon drying over $P_2O_5$ at 140° C. Nothing is said about the relative proportions.

In U.S. Pat. No. 2,803,561 alkyltrichlorosilane is hydrolyzed to the corresponding alkylsilicic acid, which is subsequently reacted with alkali metal hydroxide to give an aqueous solution of alkali metal siliconate, which is stabilized by addition of up to 10% alcohol or ketone. How the drying of the siliconate is carried out is not described. The use of the dried siliconate for the hydrophobization of gypsum is mentioned.

SUMMARY OF THE INVENTION

The invention provides a process for producing solids (S) from salts of silanols, of their hydrolysis/condensation products, or of silanols together with their hydrolysis/condensation products and cations selected from alkali metal ions in which the molar ratio of cation to silicon is from 0.1 to 3, wherein in a first step alkoxysilanes, their hydrolysis/condensation products, or alkoxysilanes together with their hydrolysis/condensation products, wherein the alkoxy group is selected from methoxy, ethoxy, 1-propoxy and 2-propoxy group, are hydrolyzed with alkali metal hydroxide and water, and in a second step the water present in the hydrolyzate and the alcohol present are evaporated out of the hydrolyzate prepared in the first step in a fixed bed, and solids (S) are obtained.

DETAILED DESCRIPTION OF THE PREFERRED EMBODIMENTS

The process differs from the prior art by the use of a fixed bed for drying. The increase in surface area achieved as a result enables rapid evaporation of the volatile constituents, especially alcohol and water, such that material adhering to the apparatus wall and agglomeration effects are largely avoided.

The fixed bed preferably consists of a pulverulent or granulated material that does not significantly impair the later use, if at all. Since the solid (S) produced in accordance with the invention preferably serves for hydrophobization of construction materials, the fixed bed used preferably comprises pulverulent or granulated construction materials, ready-to-use construction material mixtures, typical admixtures for ready-to-use construction material mixtures, solids that are inert under the production and storage conditions, or already dried siliconate, especially solids (S), where the composition of the initially charged siliconate may differ from the siliconate to be dried, the solution of which has been produced in step 1 of the process according to the invention. It is also possible to use mixtures of various solids as the fixed bed.

Examples of fixed bed materials are: potassium methylsiliconate, sodium methylsiliconate, sodium silicate (waterglass), potassium silicate, calcium hydroxide, calcium oxide, calcium silicate, calcium aluminum silicate, calcium phosphate, gypsum (calcium sulfate dihydrate), such as alabaster gypsum, α-hemihydrate, β-hemihydrate, anhydrite I, anhydrite $II_u$, anhydrite $II_s$, anhydrite III, analin, ready-to-use gypsum plaster, ready-to-use gypsum spackling compound, for example joint filler, portland cement, trass cement, white cement, iron powder, iron oxide, aluminum powder, aluminum oxide, quartz sand, glass beads, glass powder, alumina, granite sand, basalt powder, porphyry granules, potassium hydroxide, sodium hydroxide, lithium hydroxide, potassium carbonate, sodium carbonate, sodium hydrogencarbonate, sodium sulfate, calcium carbonate, chalk, dolomite powder, magnesium carbonate, magnesium oxide, talc, mica powder, sodium chloride, potassium chloride, potassium sulfate, finely divided silica, precipitated silica, silicon dioxide, methyl silica, bentonite, silica gel, polyvinyl acetate, party hydrolyzed polyvinyl acetate, polyvinyl acetate copolymers with ethylene and/or vinyl chloride and/or butene and/or vinyl laurate and/or methyl (meth)acrylate, polyvinyl alcohol, methyl cellulose, cellulose, starch, sucrose, glucose, tripotassium citrate, potassium tartrate and solids (S).

The choice of primary fixed bed material initially charged at the start of drying is guided by the field of use of the end product, because this then of course contains at least the fixed bed component initially charged. For example, for uses for hydrophobization of gypsum-containing construction materials, preference is given to using gypsum, ready-to-use gypsum mixtures or inert materials such as quartzes, silicates or chalk as primary fixed bed material.

If the fixed bed used is not the hydrolyzate from step 1 which has already been dried to give siliconate solids, especially solids (S), for example from an earlier production campaign, but rather siliconate solids of a different composition or another solid, the mass ratio of primary fixed bed used to the siliconate to be dried decides the efficacy of the end product. In order to achieve maximum hydrophobizing efficacy, a maximum proportion of dried siliconate from step 1, especially solids (S), should therefore be used as fixed bed material. The proportion of dried hydrolyzate from step 1 in the dried solids (S) is preferably at least 60%, more preferably at least 80%, especially at least 95%, based on the mass of the solids (S).

The particle sizes of the fixed bed used are preferably not more than 2 cm, more preferably not more than 1 mm, especially not more than 0.5 mm, preferably at least 0.1 μm, more preferably at least 1 μm, especially at least 10 μm.

In this case, the aqueous-alcoholic solutions of organosiliconates, the preparation of which is described, for example, in PCT/EP2011/061766 and DE 4336600, that are obtained in the hydrolysis reaction of alkoxysilanes with alkali metal hydroxide solutions are, in the second step, brought into contact with the fixed bed under conditions under which very rapid evaporation of the volatile components takes place. Surprisingly, it is possible in this procedure to avoid the intermediate formation of a highly viscous, scarcely stirrable mass and hence agglomeration to larger solids particles which are difficult to break up, so that drying is possible quickly and gently in a simple stirring unit or paddle drier. The process is very energy efficient and environmentally friendly because no azeotropic solvent is required and only the minimal required amount of water must be evaporated off. The distillates contain only alcohol and water and thus permit simple recycling of reusable materials.

Salts of organosilanols are preferably prepared in the process, there being used in the first step organoalkoxysilanes of the general formula 1

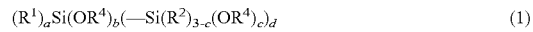

$$(R^1)_a Si(OR^4)_b (\!-\!Si(R^2)_{3-c}(OR^4)_c)_d \quad (1)$$

or their hydrolysis/condensation products, or the organosilanes of the general formula 1 together with their hydrolysis/condensation products, wherein $R^1$, $R^2$ represent a monovalent Si—C-bonded hydrocarbon radical having from 1 to 30 carbon atoms which is unsubstituted or substituted by halogen atoms, amino groups, $C_{1-6}$-alkyl or $C_{1-6}$-alkoxy or silyl groups and in which one or more non-adjacent —$CH_2$— units can be replaced by groups —O—, —S— or —$NR^3$— and in which one or more non-adjacent =CH— units can be replaced by groups —N=, $R^3$ represents hydrogen, a monovalent hydrocarbon radical having from 1 to 8 carbon atoms which is unsubstituted or substituted by halogen atoms or $NH_2$ groups, $R^4$ represents methoxy, ethoxy, 1-propoxy or 2-propoxy group, a represents the values 1, 2 or 3, and b, c, d represent the values 0, 1, 2 or 3, with the proviso that b+c≥1 and a+b+d=4.

There can also be used mixed oligomers of compounds of the general formula 1, or mixtures of those mixed oligomeric siloxanes with monomeric silanes of the general formula 1. Any silanol groups formed by hydrolysis that are present in the compounds of the general formula 1 or their oligomers are not troublesome.

$R^1$, $R^2$ can be linear, branched, cyclic, aromatic, saturated or unsaturated. Examples of amino groups in $R^1$, $R^2$ are radicals —$NR^5R^6$, wherein $R^5$ and $R^6$ can be hydrogen or a $C_1$—$C_8$-alkyl, cycloalkyl, aryl, arylalkyl, alkylaryl radical which can be substituted by —$OR^7$, wherein $R^7$ can be $C_1$—$C_8$-alkyl, aryl, arylalkyl, alkylaryl. If $R^5$, $R^6$ are alkyl radicals, non-adjacent $CH_2$ units therein can be replaced by groups —O—, —S—, or —$NR^3$—. $R^5$ and $R^6$ can also represent a ring. $R^5$ is preferably hydrogen or an alkyl radical having from 1 to 6 carbon atoms.

$R^1$, $R^2$ in the general formula 1 preferably represents a monovalent hydrocarbon radical having from 1 to 18 carbon atoms which is unsubstituted or substituted by halogen atoms or by amino, alkoxy or silyl groups. Particular preference is given to unsubstituted alkyl radicals, cycloalkyl radicals, alkylaryl radicals, arylalkyl radicals and phenyl radicals. The hydrocarbon radicals $R^1$, $R^2$ preferably have from 1 to 6 carbon atoms. Particular preference is given to the methyl, ethyl, propyl, 3,3,3-trifluoropropyl, vinyl and phenyl radicals, and most particular preference is given to the methyl radical.

Further examples of radicals $R^1$, $R^2$ are:

n-propyl, 2-propyl, 3-chloropropyl, 2-(trimethylsilyl) ethyl, 2-(trimethoxysilyl)-ethyl, 2-(triethoxysilyl)-ethyl, 2-(dimethoxymethylsilyl)-ethyl, 2-(diethoxymethylsilyl)-ethyl, n-butyl, 2-butyl-, 2-methylpropyl, tert-butyl-, n-pentyl, cyclopentyl, n-hexyl, cyclohexyl, n-heptyl, n-octyl, 2-ethyl-hexyl, n-nonyl, n-decyl, n-undecyl, 10-undecenyl, n-dodecyl, isotridecyl, n-tetradecyl, n-hexadecyl, vinyl, allyl, benzyl, p-chlorophenyl, o-(phenyl)phenyl, m-(phenyl)phenyl, p-(phenyl)phenyl, 1-naphthyl, 2-naphthyl, 2-phenylethyl, 1-phenylethyl, 3-phenylpropyl, 3-(2-aminoethyl)aminopropyl, 3-aminopropyl, N-morpholinomethyl, N-pyrrolidinomethyl, 3-(N-cyclohexyl)aminopropyl, and 1-N-imidazolidinopropyl.

Further examples of $R^1$, $R^2$ are radicals $-(CH_2O)_n-R^8$, $-(CH_2CH_2O)_m-R^9$, and $-(CH_2CH_2NH)_oH$, wherein n, m and o represent values from 1 to 10, in particular 1, 2, 3, and $R^8$, $R^9$ have the meanings of $R^5$, $R^6$.

$R^3$ preferably represents hydrogen or an alkyl radical having from 1 to 6 carbon atoms which is unsubstituted or substituted by halogen atoms. Examples of $R^3$ are listed above for $R^1$.

d preferably represents the value 0. d represents a value 1, 2 or 3 in preferably not more than 20 mol %, in particular not more than 5 mol %, of the compounds of the general formula 1.

Examples of compounds of the general formula 1 wherein a=1 are:

$MeSi(OMe)_3$, $MeSi(OEt)_3$, $MeSi(OMe)_2(OEt)$, $MeSi(OMe)(OEt)_2$, $MeSi(OCH_2CH_2OCH_3)_3$, $H_3C-CH_2-CH_2-Si(OMe)_3$, $(H_3C)_2CH-Si(OMe)_3$, $CH_3CH_2CH_2CH_2-Si(OMe)_3$, $(H_3C)_2CHCH_2-Si(OMe)_3$, tBu-Si(OMe)$_3$, PhSi(OMe)$_3$, PhSi(OEt)$_3$, $F_3C-CH_2-CH_2-Si(OMe)_3$, $H_2C=CH-Si(OMe)_3$, $H_2C=CH-Si(OEt)_3$, $H_2C=CH-CH_2-Si(OMe)_3$, $Cl-CH_2CH_2CH_2-Si(OMe)_3$, n-hexyl-Si(OMe)$_3$, cy-Hex-Si(OEt)$_3$, cy-Hex-CH$_2$-CH$_2$-Si(OMe)$_3$, $H_2C=CH-(CH_2)_9-Si(OMe)_3$, $CH_3CH_2CH_2CH_2CH(CH_2CH_3)-CH_2-Si(OMe)_3$, hexadecyl-Si(OMe)$_3$, $Cl-CH_2-Si(OMe)_3$, $H_2N-(CH_2)_3-Si(OEt)_3$, cyHex-NH-(CH$_2$)$_3$-Si(OMe)$_3$, $H_2N-(CH_2)_2-NH-(CH_2)_3-Si(OMe)_3$, $O(CH_2CH_2)_2N-CH_2-S(OEt)_3$, PhNH-CH$_2$-Si(OMe)$_3$, hexadecyl-SiH$_3$, $(MeO)_3Si-CH_2CH_2-Si(OMe)_3$, $(EtO)_3Si-CH_2CH_2-Si(OEt)_3$, $(MeO)_3SiSi(OMe)_2Me$, and $MeSi(OEt)_2Si(OEt)_3$.

Preference is given to MeSi(OMe)$_3$, MeSi(OEt)$_3$, $(H_3C)_2CHCH_2-Si(OMe)_3$ and PhSi(OMe)$_3$, with methyltrimethoxysilane and its hydrolysis/condensation products being particularly preferred.

Examples of compounds of the general formula 1 wherein a=2 are:

Me$_2$Si(OMe)$_2$, Me$_2$Si(OEt)$_2$, Me$_2$Si(OCH(CH$_3$)$_2$)$_2$, MeSi(OMe)$_2$CH$_2$CH$_2$CH$_3$, Et$_2$Si(OMe)$_2$, Me$_2$Si(OCH$_2$CH$_2$OCH$_3$)$_2$, MeSi(OMe)$_2$Et, $(H_3C)_2CH-Si(OMe)_2Me$, Ph-Si(OMe)$_2$Me, t-Bu-Si(OMe)$_2$Me, Ph$_2$Si(OMe)$_2$, PhMeSi(OEt)$_2$, MeEtSi(OMe)$_2$, $F_3C-CH_2CH_2-Si(OMe)_2Me$, $H_2C=CH-Si(OMe)_2Me$, $H_2C=CH-CH_2-Si(OMe)_2Me$, $Cl-CH_2CH_2CH_2-Si(OMe)_2Me$, cy-Hex-Si(OMe)$_2$Me, cy-Hex-CH$_2$-CH$_2$-Si(OMe)$_2$Me, $H_2C=CH-(CH_2)_9-Si(OMe)_2Me$, $Cl-CH_2-SiMe(OMe)_2$, $H_2N-(CH_2)_3-SiMe(OEt)_2$, cyHex-NH-(CH$_2$)$_3$-SiMe(OMe)$_2$, $H_2N-(CH_2)_2-NH-(CH_2)_3-SiMe(OMe)_2$, $O(CH_2CH_2)_2N-CH_2-SiMe(OMe)_2$, PhNH-CH$_2$-SiMe(OMe)$_2$, $(MeO)_2MeSi-CH_2CH_2-SiMe(OMe)_2$, $(EtO)_2MeSi-CH_2CH_2-SiMe(OEt)_2$, $(MeO)_2MeSiSi(OMe)_2Me$, MeSi(OEt)$_2$SiMe(OEt)$_2$, MeCl$_2$SiSiMeCl$_2$, Me$_2$Si(OMe)Si(OMe)$_3$, Me$_2$Si(OMe)Si(OMe)Me$_2$, Me$_2$Si(OMe)SiMe$_3$, and Me$_2$Si(OMe)SiMe(OMe)$_2$.

Preference is given to Me$_2$Si(OMe)$_2$, Me$_2$Si(OEt)$_2$, MeSi(OMe)$_2$CH$_2$CH$_2$CH$_3$ and Ph-Si(OMe)$_2$Me, with Me$_2$Si(OMe)$_2$ and MeSi(OMe)$_2$CH$_2$CH$_2$CH$_3$ being particularly preferred.

Me denotes the methyl radical, Et denotes the ethyl radical, Ph denotes the phenyl radical, t-Bu denotes the 2,2-dimenthylethyl radical, cy-Hex denotes the cyclohexyl radical, hexadecyl denotes the n-hexadecyl radical.

Preferably a=1 or 2.

In particular, at least 50%, preferably at least 60%, more preferably at least 70%, and not more than 100%, preferably not more than 90%, more preferably not more than 80%, of all the radicals $R^1$ in the compounds of the general formula 1 or their hydrolysis/condensation products are methyl radicals, ethyl radicals or propyl radicals.

The alkali metal hydroxide used is preferably selected from lithium, sodium and potassium hydroxide.

The amount of alkali metal hydroxide used in the first step is preferably so chosen that the molar ratio of cation to silicon is at least 0.2, preferably at least 0.4, more preferably at least 0.5, and most preferably at least 0.6, and not more than 3.0, preferably not more than 1.0, more preferably not more than 0.8, and most preferably not more than 0.7.

The hydrolyzate formed in the first step may be present in the form of a solution and/or a suspension in which the silanolate salt is present in undissolved form. The hydrolyzate formed in the first step may also be concentrated to a suspension by evaporation before it is used in step 2. Mixtures of alcoholic-aqueous mixtures of different silanolate salts can also be used in the second step, in which case one or more alcohols can be present.

The purpose of step 2 is to remove the volatile constituents—principally alcohol and the water present or any water formed by condensation processes in the drying process—from the mixture so rapidly that no tacky, viscous intermediates occur. The drying conditions in the fixed bed are therefore preferably selected such that the volatile constituents having the highest boiling point evaporate immediately or very quickly on contact with the fixed bed. In order to ensure this, temperature and optionally pressure in the course of drying are set accordingly.

If organoalkoxysilanes of the general formula 1 are used in the first step, the fixed bed or wall temperature, that is to say the highest temperature with which the mixture to be dried comes into contact, is preferably so chosen that thermal decomposition of the reaction mixture is largely avoided within the total drying time during step 2. To that end, the time to the maximum rate of thermal decomposition under adiabatic conditions (=Time to Maximum Rate=$TMR_{ad}$) is conventionally determined at different temperatures by means of DSC measurements on the hydrolyzate mixture, and the maximum temperature is chosen at which, optionally while observing a safety interval, there is no risk of uncontrolled exothermic decomposition within the period of the thermal load during drying. The fixed bed or wall temperature is preferably so chosen that the $TMR_{ad}$ is at least 200%, preferably at least 150%, and more preferably at least 100%, of the drying time. In order to achieve a high space-time yield, as high a temperature as possible in step 2 is therefore to be sought. The fixed bed or wall temperature in step 2 is preferably at least 70° C., more preferably at least 90° C., in particular at least 100° C., and preferably not more than 200° C., more preferably not more than 160° C., and in particular not more than 140° C., provided that no disruptive thermal decomposition occurs at those temperatures. The temperature can remain constant during step 2 or can follow an ascending or descending gradient, a constant operation mode being preferred. To avoid thermal decomposition, it is advantageous to reduce the pressure during the drying in step 2 compared to the pressure of the surrounding atmosphere. Preferably, a pressure of not more than 800 hPa, more preferably not more than 200 hPa, and especially not more than 20 hPa, preferably at least 0.01 hPa, more preferably at least 1 hPa, and especially at least 5 hPa, is established. In order to achieve a maximum space-time yield, preferably both the maximum fixed bed temperature at which no significant thermal decomposition is to be expected during the drying time is selected, and the pressure during the drying process is set to the technically and economically achievable minimum. The dosage rate of the hydrolyzate from step 1 to the fixed bed is preferably selected such that the formation of agglomerates can be very substantially avoided. Also possible, but not preferable, is a two-stage or multistage process in which a suspension is first produced from the hydrolyzate solution from step 1 and fixed bed, which is then dried in a downstream step.

Preference is given to drying down to a residual moisture content measured at 120° C. in the solids (S) of not more than 3% by weight, more preferably not more than 1% by weight, and especially not more than 0.5% by weight, based on the starting weight. Preferably, drying is conducted with exclusion of oxygen, especially under an inert gas atmosphere, for example of nitrogen, argon, helium.

To accelerate the drying process, the fixed bed can be fluidized with the aid of a gas, for example inert gas such as nitrogen or vapor, for example steam—in the extreme case up to the formation of a fluidized bed.

The process can be carried out in batch mode, for example using a stirred tank or paddle drier with a distillation head, as is conventional in multipurpose installations. In this case, the fixed bed is initially charged under the desired drying conditions—preferably heated to a temperature above room temperature and under reduced pressure—and the hydrolyzate solution from step 1 is metered onto the fixed bed. The metered addition can be effected via simple dropwise addition or spraying, for example with the aid of nozzles, optionally with parallel injection of inert gas. In order to achieve very homogeneous distribution and constant renewal of the surface of the fixed bed, the fixed bed is preferably kept in motion by constant stirring during the drying operation. After the desired amount has been dried—for example when the maximum fill level of the apparatus has been attained—solids (S), especially in the form of granules or powder, are withdrawn, for example, by expelling them through an immersed tube or discharging them through the base valve.

In contrast to direct heating, for example by means of electrical resistance heating, induction heating, microwave heating, firing/hot gas heating, it is advantageous in the case of indirect heat transfer by means of heat transfer media, for example steam, water, heat transfer oil, from the point of view of the process and for time reasons, if step 2 proceeds at constant temperature.

Owing to the low level of fouling, it is not usually necessary during production campaigns to clean the reactor of solids residues between the individual batches. If cleaning should nevertheless be required, for example at the end of the campaign, it is readily possible, inexpensively and without harmful emissions, simply by rinsing or optionally flushing the installation with water. A continuous process in a tubular reactor or a mixing/conveying unit such as a kneader or a single-screw or twin-screw extruder or a horizontal paddle drier is likewise possible and is advantageous for large-scale production. If the drying is conducted under reduced pressure, recharging of fixed bed material and the discharge for dispensing or into storage vessels are preferably effected via a pressure lock. Preferably, the product is cooled to ambient temperature or slightly above upstream of or in the region of the discharge zone. Preferably, a continuous process is conducted in such a way that the desired final drying level is attained within a single process step. In addition, it is also possible to conduct multistage drying processes with several series-connected continuous or semi-batchwise process steps. For example, it is possible first to granulate a siliconate partly dried by means of a fixed bed in the first step and then to dry it to the desired drying level to give the solid (S) in a pan dryer. A constant product quality and composition can be achieved, for example, by recharging the fixed bed by recycling a substream of the solid (S) after the drying, or of a precursor thereof.

In addition, further additives such as, for example, flow-regulating agents or anticaking agents can be added before, during or after the process according to the invention. This is done for example, by metered addition to the fixed bed in the second step.

If desired, the solids (S) obtained by the process according to the invention can be comminuted or compressed to form coarser particles or shaped bodies, for example granules, pellets, briquettes, and then screened and graded. The fractions which are separated out as undersize or oversize can thus, for example, be recycled as fixed bed material. Preferably, the solids (S) are produced in the form of powder or granules.

All the above symbols of the above formulae have their meanings in each case independently of one another. In all formulae, the silicon atom is tetravalent.

In the examples and comparative examples which follow, all amounts and percentages are based on weight, unless indicated otherwise, and all reactions are carried out at a pressure of 1000 hPa (abs.).

EXAMPLE 1

Process According to the Invention for Drying a Potassium Methyl Siliconate (K:Si=0.65:1)

In step 1, a hydrolyzate H1 is prepared analogously to Example 1 of DE 4336600 from one molar equivalent of methyltrimethoxysilane (prepared from 1 molar equivalent of methyltrichlorosilane and 2*1.5 molar equivalents of methanol), 0.65 molar equivalent of potassium hydroxide and 3.5 molar equivalents of water (in the form of a 37% potassium hydroxide solution).

Solids content=39 wt. % (determined at 160° C. using a solids content balance HR73 Halogen Moisture Analyzer from Mettler Toledo, contains according to NMR 46.5 wt. % methanol and 14.5 wt. % water).

In order to determine the variation in the thermal stability during the drying process, a sample of that mixture is devolatilized in succession at 120° C. first under normal pressure and then with a pressure reduction to 5 hPa. Samples for DSC measurements are taken at various stages of the process. According to those measurements, the moist but already solid distillation residue has the lowest onset temperature (about 174° C.) and the highest decomposition energy (about 806 kJ/kg).

In order to determine the Time to Maximum Rate (TMR$_{ad}$) of the thermal decomposition under adiabatic conditions, DSC measurements of that residue are carried out with different heating rates in pressure-resistant stainless steel crucibles under nitrogen in a temperature range between room temperature and 400° C. Evaluation is made by a so-called "isoconversion" method with conversion-dependent activation energy according to S. Vyzovkin, C. A. Wright, Model-free and model-fitting approaches to kinetic analysis of isothermal and nonisothermal Data, Thermochim. Acta, 1999, 340-341, 53-68. The evaluation is carried out using the program AKTS, Thermal Kinetics, Version 3.24 according to B. Roduit, Ch. Borgeat, B. Berger, P. Folly, B. Alonso, J. N. Aebischer, F. Stoessel, Advanced Kinetic Tools for the Evaluation of Decomposition Reactions, J. Thermal Anal. and Calor. 2005, 80, 229-236. The TMR$_{ad}$ is calculated for different temperatures using the conversion-dependent activation energy.

There is accordingly obtained a TMR$_{ad}$ of >24 h at 118° C., of >20 h at 120° C. and of >8 h at 130° C. On the basis of these data, a wall and fixed bed temperature of not more than 120° C. is established for the drying process.

Drying of a potassium methyl siliconate solution

A nitrogen-inertized 500 ml 5-neck glass flask with dropping funnel, paddle stirrer, thermometer and distillation system is initially charged with 50 g of the siliconate powder dried for the abovementioned DSC analyses and heated to 120° C. with stirring in an oil bath, in the course of which the pressure is reduced to 5 hPa by means of a vacuum pump. Subsequently, 113 g of the hydrolyzate H1 are metered in from the dropping funnel within one hour. In the course of dropwise addition to the hot fixed bed, the volatile constituents evaporate instantaneously, which leads to significant dust formation in the flask. In the course of this, 69.3 g of clear colorless distillate collect in the receiver. The amount of solids weighed in is about 90 g.

Thus, 91% of the solids content present in the siliconate solution H1 is converted to a dry powder. The solids content thereof is 99.8% (determined with the HR73 Halogen Moisture Analyzer solids content balance from Mettler Toledo at 160° C.); it dissolves in water to give a 50% solution.

EXAMPLE 2

Process According to the Invention for Drying a Potassium Methyl Siliconate (K:Si=0.65:1) in the Presence of a Silica A nitrogen-inertized 500 ml 5-neck glass flask with dropping funnel, paddle stirrer, thermometer and distillation system is initially charged with 25 g of the siliconate powder dried for the abovementioned DSC analyses and 2.5 g of a silica isolated from the filter of a residue incineration system, and heated to 120° C. with stirring in an oil bath, in the course of which the pressure is reduced to 5 hPa by means of a vacuum pump. Subsequently, 56 g of the hydrolyzate H1 are metered in from the dropping funnel within 25 minutes. In the course of dropwise addition to the hot fixed bed, the volatile constituents evaporate instantaneously, which leads to significant dust formation in the flask. In the course of this, 34 g of clear colorless distillate collect in the receiver. 10 minutes after the metered addition has ended, the solids content of a powder sample withdrawn is 98.4% (determined with the HR73 Halogen Moisture Analyzer solids content balance from Mettler Toledo at 160° C.). After a further 10 minutes, the solids content of a powder sample withdrawn is 99.5%. The amount of solids weighed in is about 46 g. Thus, 85% of the solids content present in the siliconate solution H1 is converted to a dry powder. It dissolves in water to give a 50% solution.

EXAMPLE 3-6

Process According to the Invention for Drying a Potassium Methyl Siliconate (K:Si=0.65:1) in the Presence of Various Fixed Bed Materials The drying step in example 1 is repeated in each case, except that, rather than the dried siliconate powder as the fixed bed, the same proportion in each case of alabaster gypsum (3), kieselguhr (Celite 545) (4), aluminum oxide (5) and tylose (methyl cellulose) (6) is initially charged. In all cases, free-flowing solids are obtained, and each of these was mixed into commercially available gypsum plasters (KNAUF Maschinenputz MP75, water/gypsum factor 0.60, KNAUF Goldband, water/gypsum factor 0.67) in an amount of 0.4% by weight. The water absorption determined to DIN EN 520 of gypsum specimens produced therewith was well below 3% by weight in each case. The efficacy was thus within the range of the solid from example 1, meaning that it was not impaired by the inert constituents of the fixed bed.

The invention claimed is:

1. A process for producing alkali metal organosiliconate-containing solids from salts of silanols, of silanol hydrolysis and/or condensation products, or of silanols together with silanol hydrolysis and/or condensation products, and alkali metal cations in which the molar ratio of alkali metal cation to silicon is from 0.1 to 3,
wherein in a first step, alkoxysilanes, alkoxysilane hydrolysis and/or condensation products, or alkoxysilanes together with alkoxysilane hydrolysis and/or condensation products, wherein the alkoxy group is selected from the group consisting of methoxy, ethoxy, 1-propoxy, 2-propoxy groups, and mixtures thereof, are hydrolyzed with alkali metal hydroxide and water to form a hydrolysate,
and in a second step, water present in the hydrolyzate and alcohol present in the hydrolysate are evaporated out of the hydrolyzate prepared in the first step in a dryer containing a bed of pulverulent or granulated solids, and an alkali metal organosiliconate-containing solid product also containing the pulverulent or granulated solids from the bed is removed from the dryer.

2. The process of claim 1, wherein the bed of pulverulent or granulated solids comprises at least one pulverulent or granulated material selected from the group consisting of potassium methylsiliconate, sodium methylsiliconate, sodium silicate, potassium silicate, calcium hydroxide, calcium oxide, calcium silicate, calcium aluminum silicate, calcium phosphate, gypsum, ready-to-use gypsum plaster, ready-to-use gypsum spackling compound, portland cement, trass cement, white cement, iron powder, iron oxide, aluminum powder, aluminum oxide, quartz sand, glass beads, glass powder, alumina, granite sand, basalt powder, porphyry granules, potassium hydroxide, sodium hydroxide, lithium hydroxide, potassium carbonate, sodium carbonate, sodium hydrogencarbonate, sodium sulfate, calcium carbonate, chalk, dolomite powder, magnesium carbonate, magnesium oxide, talc, mica powder, sodium chloride, potassium chloride, potassium sulfate, finely divided silica, precipitated silica, silicon dioxide, methyl silica, bentonite, silica gel, polyvinyl acetate, party hydrolyzed polyvinyl acetate, polyvinyl acetate copolymers with ethylene and/or vinyl chloride and/or butene and/or vinyl laurate and/or methyl (meth)acrylate, polyvinyl alcohol, methyl cellulose, cellulose, starch, sucrose, glucose, tripotassium citrate, and potassium tartrate.

3. The process of claim 1, wherein the bed solids are selected from the group consisting of construction materials, ready-to-use construction material mixtures, admixtures for ready-to-use construction material mixtures, inert solids, dried siliconates, and mixtures thereof.

4. The process of claim 1, wherein previously prepared alkali metal organosiliconate solids are used as the fixed bed.

5. The process of claim 1, wherein the particle size of the pulverulent or granulated solids in the bed is 1 μm to 1 mm.

6. The process of claim 1, wherein in the first step, the organoalkoxysilanes are of the formula 1:

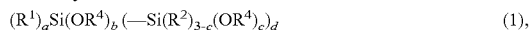

are hydrolysis and/or condensation products of organoalkoxysilanes of the formula 1, or are organoalkoxysilanes of the general formula 1 together with hydrolysis and/or condensation products of organoalkoxysilanes of the formula 1, wherein $R^1, R^2$ represent a monovalent Si—C-bonded hydrocarbon radicals having from 1 to 30 carbon atoms which is unsubstituted or substituted by halogen atoms, amino groups, $C_{1-6}$-alkyl or $C_{1-6}$-alkoxy or silyl groups and in which one or more non-adjacent —$CH_2$— units are optionally replaced by groups —O—, —S—, or —$NR^3$— and in which one or more non-adjacent =CH— units are optionally replaced by the group —N=, $R^3$ each individually is hydrogen, or a monovalent hydrocarbon radical having from 1 to 8 carbon atoms which is unsubstituted or substituted by halogen atoms or $NH_2$ groups, $R^4$ each individually is a methoxy, ethoxy, 1-propoxy or 2-propoxy group, a is 1, 2 or 3, and b, c, and d are 0, 1, 2 or 3, with the proviso that $b+c \geq 1$ and $a+b+d=4$.

7. The process of claim 6, wherein $R^1$ and $R^2$ are hydrocarbon radicals having from 1 to 6 carbon atoms.

8. The process of claim 6, wherein d has a value of 1, 2 or 3 in not more than 20 mol % of the compounds of the formula 1.

9. The process of claim 1, wherein the fixed bed temperature in the second step is from 70° C. to 200° C.

10. The process of claim 1, wherein the pressure in the second step is from 1 hPa to 200 hPa.

11. The process of claim 1, wherein the bed of pulverulent or granulated solids is fluidized.

12. The process of claim 1, wherein the bed of pulverulent or granulated solids is stirred.

13. The process of claim 1, wherein the bed of pulverulent or granulated solids is contained in a paddle dryer.

14. The process of claim 1, wherein the solid product is further dried in a downstream dryer.

15. The process of claim 1, wherein a residual moisture content of the solid product is ≤3% by weight at 120° C. based on the weight of the solid product.

16. The process of claim 14, wherein a residual moisture content of the solid product is ≤3% by weight at 120° C. based on the weight of the solid product.

17. The process of claim 1, wherein a residual moisture content of the solid product is ≤1% by weight at 120° C. based on the weight of the solid product.

18. The process of claim 14, wherein a residual moisture content of the solid product is ≤1% by weight at 120° C. based on the weight of the solid product.

* * * * *

UNITED STATES PATENT AND TRADEMARK OFFICE
CERTIFICATE OF CORRECTION

PATENT NO. : 9,200,013 B2
APPLICATION NO. : 14/355778
DATED : December 1, 2015
INVENTOR(S) : Michael Stepp et al.

Page 1 of 1

It is certified that error appears in the above-identified patent and that said Letters Patent is hereby corrected as shown below:

In the claims

Column 11, Line 1, Claim 2:

Delete "party" and
Insert -- partly --.

Signed and Sealed this
Nineteenth Day of April, 2016

Michelle K. Lee
*Director of the United States Patent and Trademark Office*